United States Patent [19]

Runge

[11] Patent Number: 5,114,932
[45] Date of Patent: May 19, 1992

[54] HYPEROSMOLAR OXYREPLETE HEMOSUBSTITUTE

[76] Inventor: Thomas M. Runge, 2630 Exposition Blvd., Austin, Tex. 78703

[21] Appl. No.: 620,539

[22] Filed: Nov. 30, 1990

[51] Int. Cl.⁵ .................. A61K 31/66; A61K 31/70
[52] U.S. Cl. ....................... 514/58; 530/385; 514/6; 514/832; 514/833; 514/23; 514/60; 514/769; 514/777
[58] Field of Search ............. 514/6, 832, 833, 23, 514/60, 769, 777, 58; 530/385

[56] References Cited

U.S. PATENT DOCUMENTS

| | | | |
|---|---|---|---|
| 3,679,795 | 7/1972 | DeSomer et al. | 514/25 |
| 3,911,915 | 10/1975 | Seifter et al. | 514/23 |
| 3,928,574 | 12/1975 | Phillips | 514/23 |
| 3,937,821 | 2/1976 | Irikura et al. | 514/23 |
| 4,740,594 | 4/1988 | Mauzac et al. | 514/833 |
| 4,757,052 | 7/1988 | Markov | 514/833 |
| 4,866,096 | 9/1989 | Schweighardt | 514/832 |
| 4,873,230 | 10/1989 | Belzer et al. | 514/832 |
| 4,908,350 | 3/1990 | Kramer et al. | 514/2 |
| 4,927,806 | 5/1990 | Kramer et al. | 514/832 |

FOREIGN PATENT DOCUMENTS

| | | |
|---|---|---|
| 0142125 | 5/1985 | European Pat. Off. |
| 2837067 | 5/1979 | Fed. Rep. of Germany |
| 862418 | 7/1982 | U.S.S.R. |

*Primary Examiner*—Ronald W. Griffin
*Attorney, Agent, or Firm*—James G. O'Boyle; Isaac A. Angres

[57] ABSTRACT

New blood substitutes are described having osmolarities greater than normal blood. The new blood substitues typically comprise a physiologically acceptable fluid electrolyte solution, a physiologically acceptable agent capable of increasing the osmolarity of the blood substitute to a value greater than normal blood, an oxygen carrying substance, and a sufficient amount of water to achieve the desired osmolarity. The blood substitutes of the present invention have osmolarities in the range of 500-800 milliosmoles per liter.

14 Claims, No Drawings

HYPEROSMOLAR OXYREPLETE HEMOSUBSTITUTE

The present invention relates to a novel hyperosmolar oxyreplete blood substitute, its method of making and method of use.

DESCRIPTION OF THE PRIOR ART

The use of blood substitutes for replacing blood during certain medical procedures have been known for several years. In U.S. Pat. No. 4,173,654, there is disclosed an artificial blood substitute comprising a perfluorocarbon, a surfactant, a physiologically acceptable aqueous carrier solution, and effective amounts of osmotic and oncotic agents.

U.S. Pat. No. 4,186,253 teaches a perfusate that utilizes a modified Ringer's solution, an albumin solution, a perfluorocarbon and an emulsifier.

U.S. Pat. No. 4,397,870 discloses an artificial blood composition containing an emulsifier, Ringer's solution and a perfluorohydrocarbon compound.

U.S. Pat. No. 3,962,439 features an artificial blood substitute comprising perfluorohydrocarbon compounds and a physiologically acceptable aqueous solution such as Ringer's solution.

U.S. Pat. No. 3,937,821 relates to a plasma substitute comprising hydroxyethylstarch, physiologically acceptable electrolytes, glucose and water.

U.S. Pat. No. 4,423,077 discloses an emulsion of perfluorocarbon compounds in a physiologically acceptable medium.

Other patents of interest relating to blood substitutes include the following U.S. Pat. Nos.: 4,423,061; 4,439,424; 4,866,096; 4,895,876; 4,526,715; 4,529,719; 4,584,130; 4,777,244 and 4,920,194.

None of the above patents discloses a blood substitute having the properties of hyperosmolarity and its use to prevent anasarca as well as memory loss in patients undergoing cardiopulmonary bypass surgery.

BACKGROUND OF THE INVENTION

The use of blood substitutes in the medical field is widely practiced and, more particularly, in instances in which blood is not available when it is preferable to use a substance other than blood, use of animal blood as a blood substitute is considered hazardous primarily because of incompatibility. Typical instances wherein human blood transfusion is required include, surgery, injury with bleeding, gastrointestinal hemorrhage and diffuse hemorrhagic disorders of various types. Also of interest are situations such as military battles wherein blood transfusions are required in the battlefield.

A widely performed surgery requiring blood is cardiac surgery, and cardiac surgery requiring cardiopulmonary bypass requires large amounts of blood for the cardiopulmonary bypass hardware, or if blood is not used in the cardiopulmonary bypass system, some other type of volume replacement is essential.

During cardiopulmonary bypass for cardiac surgery, the patient's total blood volume of approximately 5 or 6 liters in an adult is removed from the right atrium and passed through a bubble oxygenator by gravity flow or through a membrane oxygenator by a pump and then returned to the patient usually via the thoracic aorta; the functions of both the patient's heart as well as the patient's lungs are assumed by the cardiopulmonary bypass system. With the cardiopulmonary bypass system functioning, the patient no longer requires the functioning of his own heart and lungs, the chest cavity can now be entered, the lungs can be deflated if necessary for proper exposure of the operative field, and the heart can be opened and repaired.

However, there are known complications with surgery requiring cardiopulmonary bypass which are quite familiar to the medical profession, and understood, to a degree. For example, it is almost unheard of for a patient or an animal to survive after more than 6, or at the most, 12 hours of cardiopulmonary bypass. Fortunately most patients require much shorter periods of time on bypass, most now probably no greater than 1 hour, many less, some even as short a time as 20 minutes or even 15 minutes "on pump". Excellent tabulation of the complications of the procedure have been tabulated in man, always of course influenced by the surgery itself, so that it is not possible to differentiate clearly the effect of cardiopulmonary bypass itself upon morbidity and mortality, from the effect of the particular surgical procedure upon these two factors. But in animal studies, the morbidity and mortality of cardiopulmonary bypass alone, can be more clearly identified.

There is room for improvement in cardiopulmonary bypass procedure which had its application in man in the early 1950's. A sensitive indicator of a potential problem is current data from multi-institutional studies of a degree of memory deficit, perhaps permanent, and seemingly relatively common, especially in patients over age 60 or thereabouts, who undergo surgery utilizing cardiopulmonary bypass.

As the 6 or so liters of the patient's blood is allowed to enter the cardiopulmonary bypass system of biocompatible tubing, oxygenator, pump, heat exchanger and arterial filter, it is essential that this system be completely devoid of air, and that it contain a "priming fluid" to replace all air in the system, all air in the items noted above, and some of the air in the "venous reservoir" of the system. The volume of this priming fluid in the average adult case will be about 2.0 liters, perhaps a little more.

In the past, blood has been used as a priming fluid but for various reasons is no longer used at least not totally; and a degree of "hemodilution" is preferred at most surgical centers. Hemodilution reduces viscosity of the blood, currently considered an advantage in relation to blood flow. Currently it is common practice to prime the system with sterile water to which has been added those elements of blood consisting of molecules, other than protein, red blood cells, white blood cells and platelets.

A solution containing the above components is referred to as a physiologic crystalloid priming solution. If some, but not all, of the normal blood crystalloids are omitted, the solution is referred to simply as a crystalloid prime.

The crystalloid prime does not contain albumin, globulin, or other blood proteins, and therefore its colloid osmotic pressure is missing, although it is normo-osmolar in respect to crystalloids. There is, however, a problem in this regard, and there is a second problem as related to the oxygen carrying capacity of this priming fluid.

The osmolarity of normal human plasma is about 303 mOsmoles per liter of water, and standard crystalloid priming solutions for cardiopulmonary bypass often approximate this value. However, these solutions contain no protein, hence these primes possess no colloid osmotic pressure, differing in this way from normal human blood which contains about 7.0 grams per cent protein, mainly albumin and globulin, and the effect upon fluid transfer from the intravascular space to the intracellular space is very great. Fluid accumulation in the patient has been estimated at 1.0 or more liters per square meter of body surface area per hour of bypass, with additional fluid retention persisting into the postoperative patients not receiving blood replacement.

Water retention and fluid accumulation in the body (a condition known in the medical field as anasarca) can be reduced by the administration of colloidal substitutes such as dextran, hydroxyethyl-starch and others.

The fact is, however, that cardiopulmonary bypass is known to be associated with tendency to interstitial water retention, and perhaps intracellular water retention, the net effect of which may be related to morbidity associated with this procedure.

The normal hematocrit of most patients (the packed red cell volume) is about 40 to 45%. With hemodilution induced by crystalloid prime, most surgical centers employ hemotocrit levels of 20 to 25% while on pump, which means that the oxygen carrying capacity of each milliliter of blood traversing the patient's circulatory tree is now capable of carrying about 50% as much oxygen as before hemodilution. It may be that this reduction in oxygen carrying capacity of the blood and perhaps aggravated by anasarca and its aggravation of impaired oxygen transfer to the cell is the component, or one of the components in the reduced memory currently being reported in a significant percentage of cardiopulmonary bypass procedure patients. This diminished oxygen carrying capacity can be ameliorated by the addition of an oxyreplete substance such as perfluorochemicals.

Basically, an artificial replacement fluid should have the following properties to be feasible:

It should function for at least several hours as well as normal blood having a hematocrit of about 45%.

It should not be toxic.

It should be sterile and pyrogen free.

It should be free of any antigens, i.e., it should not activate the body's immune system; nor should it require any blood typing analysis.

It should have a reasonable "shelf-life" at least as long as, or longer than, fresh whole blood.

While many different approaches have been disclosed for providing a viable oxygen transport system, for instance, U.S. Pat. Nos. 3,937,821; 3,962,439; 4,173,654; 4,186,253; 4,397,870 and 4,423,077, none of these patents discloses a hyperosmolar blood substitute for preventing anasarca and enhancing oxygenation in a patient undergoing cardiopulmonary bypass surgery.

Because of the problems associated with cardiopulmonary bypass surgery such as anasarca and reduced memory as described above, after considerable research and experimentation applicant has discovered new blood substitutes which substantially reduce or eliminate the above problems associated with said surgery.

The prior art is silent regarding a hyperosmolar blood substitute which has increased oxygen carrying capacity.

SUMMARY OF THE INVENTION

The present invention represents new blood substitute compositions comprising a physiologically acceptable fluid electrolyte solution, a physiologically acceptable agent capable of increasing the osmolarity of the blood substitute to a value greater than normal blood, and oxygen carrying substance and sufficient amount of water to achieve the desired osmolarity.

A principal object of the present invention is a blood substitute having an effective osmolarity greater than normal blood.

Another object of the present invention is to provide blood substitutes in the hyperosmolar range.

A further object of the present invention is a blood substitute having osmolarities greater than 303 milliosmoles per liter.

Still another object of the present invention is a blood substitute having an osmolarity in the range of 500–800 milliosmoles per liter.

A further object of the present invention is a method for preventing anasarca in a patient undergoing cardiopulmonary bypass surgery by administering to said patient a hyperosmolar blood substitute.

An additional object of the present invention is a method for preventing memory loss in a patient undergoing cardiopulmonary bypass surgery by administering to said patient a hyperosmolar blood substitute.

A still further object of the present invention is to provide blood substitutes having hyperosmolar concentrations.

Yet another object of the present invention is to provide a hyperosmolar blood substitute with increased oxygen carrying capacity.

The present invention further contemplates a blood substitute which is closer to physiologic performance as it regards oxygen carrying capacity and reduction in its tendency to produce anasarca.

The invention further provides a hyperosmolar blood substitute by incorporation of a material capable of increasing the osmolarity of said blood substitute.

Yet still another object of the present invention is the modification of hemodiluted blood so as to increase the osmolarity of the blood to values higher than normal by the addition of a physiologic crystalloid or a synthetic crystalloid or colloid.

An additional object of the present invention further relates to raising the oxygen carrying capacity of hemodiluted blood by the addition of a synthetic oxygen carrying agent.

A further object of the present invention is to afford the option of a blood substitute with both oxygen supply capability and water retention reduction capability (colloidal effect substitute) and yet is non-biologic in composition, containing no human or animal components.

In the preferred embodiment of the present invention, the preferred agents to increase the osmolarity to a hyperosmolar range are sucrose and dextrose, although other saccharides are suitable.

The appended claims set forth those novel features which characterize the invention. However, the invention itself, as well as further objects and advantages thereof, will best be understood by reference to the following detailed description of the preferred embodiments.

DESCRIPTION OF THE PREFERRED EMBODIMENTS

The present invention is directed to a blood substitute and more particularly to a blood substitute for use in cardiopulmonary bypass surgery having hyperosmolar properties and increased oxygen carrying capacity.

The main chemical components of the blood substitute of the present invention are physiologically acceptable crystalloids or better defined as the chemical components which are present in normal blood, a physiologically acceptable agent or additional crystalloid capable of increasing the osmolarity of the blood substitute, a hemoglobin substitute which is capable of carrying oxygen and sufficient water to achieve the desired osmolarity.

The physiologically acceptable crystalloid components are those that are present in normal blood and their concentrations are very similar if not identical to those of normal blood. Physiologically acceptable crystalloid components can be viewed as the necessary inorganic ions and organic components which are present in normal blood. Inorganic components of the physiologically acceptable crystalloids are derived from salts which are compatible with the human body and required ions and their respective concentrations in milliequivalents per liter are as follows: sodium (142 mEq/L), chloride (103mEq/L), potassium (4 mEq/L), calcium (5 mEq/L), magnesium (3 mEq/L), bicarbonate (28 mEq/L), phosphate (4 mEq/L), sulfate (1 mEq/L), glucose (90 mEq/L) and amino acids (30 mEq/L). The amino acid component of the physiologic crystalloid component can be any of the naturally occurring amino acids and are selected from the group comprising: alanine, arginine, asparagine, aspartic acid, cysteine, cystine, 3,5-dibromotyrosine, 3,5-diiodotyrosine, glutamic acid, glutamine, glycine, histidine, hydroxylysine, dydroxyproline, isoleucine, leucine, lysine, methionine, phenylalanine, proline, serine, threonine, thyroxine, tryptophane, tyrosine and valine. Of course it is understood that by naturally occurring amino acid it is meant the above amino acids having the proper stereochemical and optical chemical configurations. Of the above amino acids, arginine, histidine isoleucine, leucine, lysine, methionine, phenylalanine, threonine, tryptophane and valine are all known to be essential amino acids.

The physiologically acceptable agent capable of increasing the osmolarity of the blood substitute to a range of 600 to 800 milliosmoles/liter is a disaccharide. Typical disaccharides which can be used in the practice of the present invention include (+) maltose, (+) cellobiose, (+) lactose and (+) sucrose. The preferred disaccharide for the practice of the present invention is sucrose although it should be noted that a molecule larger than dextrose and with reduced diffusibility is what is preferred to produce a blood substitute having hyperosmolar concentration. They are present at a concentration of 10% or greater or in sufficient quantity to increase the osmolarity preferably to a range of 600–800 milliosmoles per liter.

Other preferred materials which are capable of increasing the osmolarity of the blood substitutes as well as act as excellent carriers are the cylodextrins. Typical cyclodextrins are the alpha, beta and gamma cyclodextrins as well as substituted derivatives thereof such as $C_1$-$C_6$ alkyl, hydroxy $C_1$-$C_6$ alkyl, carboxy $C_1$-$C_6$ alkyl or ($C_1$-$C_6$ alkyloxycarbonyl) $C_1$-$C_6$ alkyl. Of particular interest is the use of gamma cyclodextrin and its derivatives. Preferred gamma cyclodextrin derivatives are those substituted with $C_1$-$C_3$ alkyl, hydroxy $C_2$-$C_4$ alkyl, carboxy $C_1$-$C_2$ alkyl or ($C_1$-$C_2$ alkyloxycarbonyl) $C_1$-$C_2$ alkyl or mixed ethers thereof.

Particularly preferred compounds are the methyl, ethyl, isopropyl, hydroxyethyl, hydroxypropyl, hydroxybutyl, carboxymethyl and carboxyethyl substituted gamma-cyclodextrins and further the (methyl) (hydroxyethyl), (methyl) (hydroxypropyl) and (methyl) (hydroxyethyl) (carboxymethyl) substituted gamma-cyclodextrins having an average degree of substitution (DS) or molar substitution of from 0.125 to 3, more preferably of from 0.3 to 2.

The cyclodextrins of the present invention can generally be prepared by reacting the starting gamma-cyclodextrins with an appropriate O-alkylating agent or a mixture of such agents in a concentration being selected so that the desired D.C. is obtained, said reaction is preferably conducted in a suitable solvent in the presence of an appropriate base. An appropriate O-alkylating agent is, for example, an alkyl, hydroxyalkyl, carboxyalkyl or (alkyloxycarbonyl) alkyl halide or sulfonate, e.g. methyl chloride, ethyl bromide, propyl methylsulfonate, ethyl chloroacetate, alpha-chloroacetic acid; or an oxirane, e.g. oxirane, methyloxirane. Suitable solvents are, for example, water; an alcohol or polyalcohol, e.g. methanol, ethanol, 1-propanol, 2-propanol, 1-butanol, 1,2-ethanediol, 1,2-propanediol and the like; a ketone, e.g. 2-propanone, 2-butanone, 4-methyl-2-pentanone, and the like; an ether or polyether, e.g. ethoxyethane 2-(2 propyloxy) propane, tetrahydrofuran, 1,2-dimethoxyethane and the like; and $C_1$-$C_4$-alkyloxy-$C_2$-$C_3$-alkanol and mixtures of such solvents. An appropriate base is, for example, an alkali or earth alkaline metal hydroxide, e.g. sodium hydroxide, potassium hydroxide; or an alkali or earth alkaline metal hydride or amide, e.g. sodium hydride, calcium hydride, sodium amide and the like basis.

Preferably the said O-alkylation reaction is conducted with 0.1 to 3 parts by weight or water per part by weight gamma-cyclodextrin in case there is no organic solvent used, and with 1 to 40 parts by weight organic solvent per part by weight gamma-cyclodextrin in case no water is used.

In a particularly preferred way of preparing the compounds of the present invention, the reaction mixture containing the starting gamma-cyclodextrin, the solvent, base and O-alkylating agent is heated in an autoclave at a temperature comprised between 30° and 200° C. Depending on the reactivity of the O-alkylating agent, the reaction mixture is allowed to react at this temperature for 15 minutes up to 24 hours. Subsequently, the mixture is acidified and the reaction product is isolated and purified by standard separation and purification procedures such as, for example, column chromatography, ultra filtration, centrifugation, and dried.

The compounds of the present invention can also be converted into each other. For example, the (alkyloxycarbonyl) alkyl substituted gamma-cyclodextrins may be conveniently converted to the corresponding carboxyalkyl substituted gamma-cyclodextrins following art-known saponification procedures, e.g. by treating the starting compounds with an aqueous acidic or basic solution.

Other useful cyclodextrins and derivatives can be used such as those described in U.S. Pat. Nos. 3,459,731; 4,535,152; 4,596,795; 4,727,064 and 4,764,604 whose contents are incorporated herein by reference. Cyclodextrins are believed to be particularly useful because of their ability to form inclusion complexes and because of their solubilizing activity.

The hemoglobin substitute or agent capable of carrying oxygen is another important component of the compositions of the present invention and is present in sufficient amount to produce blood prime oxygen carrying capacity of 20 volumes percent.

Materials suitable as oxygen carrying agents are perfluorinated organic derivatives. The perfluorinated organic derivatives have been under biomedical investigation since 1968 particularly because of their ability to dissolve appreciable quantities of gases, such as oxygen and carbon dioxide which are of prime importance to living organisms.

Because perfluoro compounds carry oxygen in solution, they afford opportunities that cannot be realized with oxygen-binding agents such as hemoglobin. No particular off-loading oxygen pressure is needed since oxygen freely enters and leaves the perfluoro compounds; therefore, high oxygen pressure and small particles can deliver $O_2$ under conditions not as easily dealt with using red cells. For such reasons, perfluoro-type blood replacement products are highly versatile oxygen-delivery systems; however, they must be tailored to the individual biological needs. Considerable progress has been made in a relatively short time with a small number of compounds.

The fluorinated compounds used in blood-replacement preparations are variously referred to as perfluorochemicals, perfluorocarbons, fluorocarbons, and fluorochemicals. Compounds used first in this type of work were F-tributylamine, F-2-Butyltetrahydrofuran, and F-decalin was the only perfluorocarbon later.

The perfluoro compounds are colorless and odorless organic compounds in which all hydrogens have been replaced with fluorine. Theoretically, for every hydrogen-containing organic compound there is a perfluoro analogue, and thus the number of possible compounds is enormous. However, because of certain physical properties, the number of those suitable for use in blood-replacement preparations is limited. Consideration of chemical properties is far less important.

The preferred perfluorochemical compounds of the present invention are typically perfluorocarbons which include three groups but are not limited to these groups.

The first group of the perfluorocarbon compounds used in the invention is a perfluorocycloalkane or perfluoro(alkylcycloalkane) which includes, for example, perfluoro($C_{3-5}$-alkylcyclohexanes) such as perfluoro(methylpropylcyclohexanes), perfluoro(butylcyclohexanes), perfluoro(trimethylcyclohexanes), perfluoro(ethylpropylcyclohexanes) and perfluoro(pentylcyclohexanes), perfluorodecalin, and perfluoro(dimethyldecalin) and perfluoroperhydrophenanthrene.

The second group is a perfluoro(alkylsaturatedheterocyclic compound) which includes, for example, perfluoro(alkyltetrahydropyrans) such as perfluoro(butyltetrahydropyrans), perfluoro-(pentyltetrahydropyrans) and perfluoro(hexyltetrahydropyrans); perfluoro(alkytetrahydrofurans) such as perfluoro(pentyltetrahydrofurans, perfluoro(hexyltetrahydrofurans) and perfluoro-(heptyltetrahydrofurans); perfluoro(N-alkylpiperidines) such as perfluoro(N-pentylpiperidines), perfluoro(N-hexylpiperidines) and perfluoro(N-butylpiperidine); and perfluoro(N-alkylmorpholines) such as perfluoro(N-pentylmorpholines, perfluoro(N-hexylmorpholines) and perfluoro(N-heptylmorpholines).

The third group is a perfluoro(tertiary-amine) which includes, for example, perfluorotripropylamine, perfluorotributylamines, perfluoro(diethylhexylamine), perfluoro(dipropylbutylamine) and perfluoro(diethylcyclohexylamine), and a perfluoro(dioxalkane), that is perfluoro(alkylene glycol dialkyl ether), such as perfluoro (3,8-dioxa-2,9-dimethyldecane) or perfluoro (tetramethylene glycol diisopropyl ether), perfluoro (3, 7-dioxa-2, 8-dimethylnonane) or perfluoro (trimethylene glycol diisopropyl ether) and perfluoro (4,6-dioxa-5,5-dimethylnonane) or perfluoro (isopropylene glycol di-n-propyl ether).

Additionally, compounds similar to perfluorooctylbromide and other perfluorochemicals are useful.

These perfluorochemical compounds are used alone or in a mixture of their isomers, and further of two or more kinds of the compounds may be available on the market. Alternatively, they may be produced according to the processes described, for example, in the articles of Industrial and Engineering Chemistry, Vol. 39, page 380 (1949); Journal Chemical Society, 1950, page 3617; and Advance of Fluorine Chemistry, Vol. I, page 129 (1960), or by other fluorination techniques.

The root chemical compound may be essentially completely perfluorinated to remove all hydrogens and unsaturation by a multiple stage fluorination technique. The chemical compound is first subjected to fluorination using a $CoF_3$ particulate bed operated at a temperature of approximately 275°–427° C. The chemical composition is carried through the bed with a nitrogen carrier gas at a pressure of ambient up to 2 psig nitrogen to organic ratio in the range of 10/90 to 90/10. Yields from this fluorination are typically 50 to 80% of theoretical. Alternatively, compounds from the group above are fluorinated in a Simon cell by well known technology.

Among the perfluorochemical compounds mentioned above, the most preferable ones are perfluorodecalin, perfluoro (methyldecalin) and perfluorooctylbromide owning to their more rapid excretion availability. Fluorocarbon is present in the form of an emulsion in the range of approximately 60 wt/vol percent or greater, but generally in the 60-90 wt/vol % range. The term wt/vol % as used throughout this text is based on grams of perfluorochemical divided by the total milliliters of emulsion.

A particularly useful emulsion for practicing the present invention is commerically available from Green Cross Corp., Osaka, Japan, under the trade name of FLUOSOL-DA. FLUOSOL-DA is an emulsion containing a mixture of perfluorodecalin and perfluorotripopyl-aminee. FLUOSOL-DA emulsions have been used extensively in Japan and in certain U.S. clinics that have developed protocols for specific uses with FDA approval. In addition to perfluorodecalin and perfluorotripopylamine, the FLUOSOL-DA emulsions contain a surfactant such as Pluronic F-68, yolk phospholipids, glycerol, sodium chlorida, potassium chloride, magnesium chloride, calcium chloride, sodium bicarbonate, glucose and hydroxyethyl starch.

The perfluorocarbon emulsions are typically prepared by homogenization using high pressure equipment such as the MantonGaulin homogenizer normally used at >2000 psi. Another useful method uses ultrasonic equipment, such as the Blackstone Ultrasonic generator. During emulsification, samples are removed and monitored for particle size using well-known analytical techniques such as phase microscopy or by using a Nicoli laser spectrophotometer. Emulsification is complete when physical characteristics such as optical density (using the laser spectrophotometer) remains constant. Particle size affects stability and viscosity and the length of time the particles remain in circulation; with larger particles disappearing quicker than smaller ones, desired mean particle diameter of less or equal to 0.2 micrometers enhances stability and permits the particles to traverse even the smallest capillaries.

In addition to the perfluorocarbon emulsions other oxygen carrying agents can be used. Among other suitable oxygen carrying agents, the synthetic hemoglobins are of particular value. Among the hemoglobins that can be used stroma free hemoglobin and cross-linked hemoglobin are suitable. Other useful hemoglobins are described in U.S. Pat. Nos. 4,895,876; 4,526,715; 4,529, 4,584,130; 4,777,244 and 4,920,194. Hemoglobin produced by recombinant DNA means can also be used as an oxygen carrying agent.

The recombinant hemoglobin useful in the hyperosmolar blood substitute of the present invention is manufactured as disclosed in WO 88/09179 (PCT/US88/01534) whose contents are incorporated by reference herein. Recombinant hemoglobin is typically a cell-free mutant hemoglobin method for producing the recombinant hemoglobin comprising the following steps:

(a) producing alpha globin by
  (i) introducing a recombinant DNA molecule into a suitable host other than an erythrocyte, said DNA having a fused gene comprising a first nucleotide sequence which codes on expression for an alpha globin, and a second nucleotide sequence which codes on expression for at least 10 amino acid segments of a beta globin,
  (ii) expressing alpha globin either in free form or as part of a fusion protein,
  (iii) if need be, cleaving said fusion protein at a selective cleavage site to liberate the alpha globin, and
  (iv) recovering and purifying said alpha globin;
(b) obtaining beta globin from a source other than blood; and
(c) preparing hemoglobin by combining said alpha and beta globin and a source of heme.

The hemoglobin is a cell-free biologically functional hemoglobin and is also free of erythrocyte membrane components.

Illustrative examples of the compositions of the present invention are described below.

EXAMPLES

Sterile conditions are observed during all phases of manufacture.

EXAMPLE 1

A solution containing the following physiologic crystalloids at the following concentrations is prepared: sodium (142 mEq/L); potassium (4 mEq/L); calcium (5 mEq/L); magnesium (3 mEq/L); chloride (103 mEq/L); bicarbonate (28 mEq/L); phosphate (4 mEq/L); sulfate (1 mEq/L); glucose (90 mEq/L); amino acids (30 mEqL).

To the solution containing the physiologic crystalloids there is added 10% by weight or more of sucrose so as to achieve a concentration range of 600-800 milliosmoles per liter.

The resulting solution is then mixed with a sufficient amount of FLUOSAL-DA 20% (Green Cross Corp., Osaka, Japan) so as to produce blood-prime oxygen carrying capacity of 20 volumes per cent.

Sterile or pyrogen free water is added to adjust concentrations to the desirable levels as long as the resulting osmolarities of the blood substitutes are in the hyperosmolar range.

EXAMPLE 2

Following the identical procedure of Example 1, a blood substitute is prepared wherein instead of sucrose, lactose is used.

EXAMPLE 3

Following the procedure of Example 1, a blood substitute is prepared wherein instead of sucrose, maltose is used.

EXAMPLE 4

Following the procedure of Example 1, a blood substitute is prepared wherein instead of sucrose, gamma cyclodextrin is used.

EXAMPLE 5

Following the procedure of Example 1, a blood substitute is prepared wherein instead of sucrose, hydroxypropyl gamma cyclodextrin is used.

EXAMPLE 6

Following the procedure of Example 1, a blood substitute is prepared wherein instead of FLUOSOL-DA, stroma free hemoglobin is used.

EXAMPLE 7

Following the procedure of Example 1, a blood substitute is prepared wherein instead of FLUOSOL-DA, recombinant hemoglobin is used.

EXAMPLE 8

Using the procedure of Example 1, a blood substitute is prepared using a cell free mutant hemoglobin.

The above hyperosmolar blood substitutes have excellent pharmaceutical properties when used during cardiopulmonary bypass surgery or other surgical procedures requiring blood.

In other preferred embodiments and examples of the invention, applicant has found ways to modify blood and blood substitutes in order to convert it closer to physiologic performance especially with respect to its oxygen carrying capacity and a reduction in its tendency to produce anasarca.

The modifications are accomplished by (1) increasing the osmolarity of the blood to values greater than normal, i.e., greater than 300 milliosmoles per liter by addition of a suitable physiologic crystalloid and (2) raising the oxygen carrying capacity of hemodiluted blood, commonly in the range of 50% of that of normal blood to an oxygen carrying capacity of normal oxygenated blood of about 20 volumes per cent when associated with normal hemoglobin of 14 to 15 grams per cent and normal hematocrit of 40 to 45 mg % by the addition of a synthetic oxygen carrying agent.

The inclusion of sufficient crystalloid to the prime so as to double the osmolarity from normal to 600, or maybe increase it to 800 or higher milliosmoles per liter, is of particular usefulness because of its ability to alleviate the problem of water retention.

EXAMPLE 9

To a solution containing the crystalloids of Example 1, there is added 10% or more by weight of sucrose so as to achieve a hyperosmolar crystalloid prime.

EXAMPLE 10

A hyperosmolar crystalloid prime is made as in Example 9 except instead of sucrose, lactose is used.

EXAMPLE 11

A hyperosmolar crystalloid prime is made as in Example 9 except instead of sucrose, maltose is used.

It is to be understood that the forms of the invention herewith described are to be taken as preferred examples of the same, and that various changes in the shape, size and arrangement of parts may be resorted to, without departing from the spirit of the invention or scope of the subjoined claims.

What is claimed is:

1. A blood substitute comprising an oxygen carrier and having an osmolarity greater than 303 milliosmoles per liter.

2. The blood substitute of claim 1 having an osmolarity in the range of 500-800 milliosmoles per liter.

3. The blood substitute of claim 2 having an osmolarity in the range of 600-800 milliosmoles per liter.

4. The blood substitute of claim 1 comprising a perfluorocarbon emulsion and a disaccharide.

5. A hyperosmolar blood substitute comprising an oxygen carrier and a physiologically acceptable molecule having a molecular trait less diffusible than dextrose and wherein said substitute has an osmolarity greater than 303 milliosmoles per liter.

6. The blood substitute of claim 5, wherein the oxygen carrying agent is a perfluorocarbon.

7. The blood substitute of claim 5, wherein said molecule less diffusible than dextrose is a disaccharide.

8. The blood substitute of claim 7, wherein the disaccharide is sucrose.

9. The blood substitute of claim 5, wherein the oxygen carrying substance is a synthetic hemoglobin or recombinant hemoglobin.

10. A blood substitute comprising an oxygen carrier and a cyclodextrin and wherein said substitute has an osmolarity greater than 303 milliosmoles per liter.

11. A hyperosmolar blood substitute composition comprising:
    (a) a physiologically acceptable fluid electrolyte solution;
    (b) a physiologically acceptable agent capable of increasing the osmolarity of said blood substitute to a value greater than that of protein free blood;
    (c) an oxygen carrying substance; and
    (d) a sufficient amount of water to achieve the desired osmolarity.

12. A hyperosmolar priming solution comprising:
    (a) physiologically acceptable electrolytes and
    (b) a physiologically acceptable agent capable of increasing the osmolarity of said priming solution to a value in the range of 500 to 800 milliosmoles per liter.

13. A blood substitute comprising:
    (a) a hyperosmolar priming solution; and
    (b) an oxygen carrying synthetic substance.

14. A blood substitute having an osmolarity greater than normal human blood comprising in addition to those physiologically acceptable crystalloids present in normal blood, a physiologically acceptable oxygen carrier substance selected from the group consisting of a perfluorocarbon, a synthetic hemoglobin, a recombinant hemoglobin and mixtures thereof and a physiologically acceptable disaccharide.

* * * * *